(12) United States Patent
Emery, III et al.

(10) Patent No.: US 11,771,537 B2
(45) Date of Patent: Oct. 3, 2023

(54) MELHOD FOR DYNAMICALLY GUIDING A DENTAL ORAL AND MAXILLOFACIAL PROSTHESIS

(71) Applicant: X-Nav Technologies, LLC, Lansdale, PA (US)

(72) Inventors: Robert W. Emery, III, McLean, VA (US); Scott A. Merritt, Green Lane, PA (US); Lars Hansson, Virginia Beach, VA (US)

(73) Assignee: X-Nav Technologies, LLC, Lansdale, PA (US)

( * ) Notice: Subject to any disclaimer, the term of this patent is extended or adjusted under 35 U.S.C. 154(b) by 997 days.

(21) Appl. No.: 16/582,666

(22) Filed: Sep. 25, 2019

(65) Prior Publication Data

US 2020/0100881 A1    Apr. 2, 2020

Related U.S. Application Data

(60) Provisional application No. 62/737,539, filed on Sep. 27, 2018.

(51) Int. Cl.
| | | |
|---|---|---|
| A61C 19/04 | (2006.01) | |
| G06T 7/593 | (2017.01) | |
| A61B 34/20 | (2016.01) | |
| A61C 8/00 | (2006.01) | |
| A61K 6/58 | (2020.01) | |

(52) U.S. Cl.
CPC .............. *A61C 19/04* (2013.01); *A61B 34/20* (2016.02); *A61C 8/0009* (2013.01); *G06T 7/593* (2017.01); *A61B 2034/2055* (2016.02); *A61C 8/0089* (2013.01); *A61C 8/0093* (2013.01); *A61K 6/58* (2020.01); *G06T 2207/10012* (2013.01); *G06T 2207/30036* (2013.01)

(58) Field of Classification Search
CPC .............. A61B 34/20; A61B 2034/105; A61B 2034/2048; A61B 2034/2051; A61B 2034/2055; A61B 2034/2063; A61C 8/0009; A61C 8/0048; A61C 8/0089; A61C 8/0093; A61C 19/04; A61K 6/58; G06T 7/593; G06T 2207/10012; G06T 2207/30036
USPC ....................................................... 433/174
See application file for complete search history.

(56) References Cited

U.S. PATENT DOCUMENTS

| | | | | |
|---|---|---|---|---|
| 9,402,691 | B2 * | 8/2016 | Merritt ..................... | A61B 6/14 |
| 9,844,324 | B2 * | 12/2017 | Merritt ............... | A61B 1/00148 |
| 9,943,374 | B2 * | 4/2018 | Merritt ..................... | G06T 7/74 |
| 2006/0269902 | A1 * | 11/2006 | Weissman ............. | A61C 8/0048 |
| | | | | 433/173 |
| 2009/0226857 | A1 * | 9/2009 | Grant .................... | A61C 8/0069 |
| | | | | 433/174 |
| 2015/0086939 | A1 * | 3/2015 | Fisker .................. | A61C 13/082 |
| | | | | 433/29 |
| 2015/0111172 | A1 * | 4/2015 | Jung ........................ | A61C 5/77 |
| | | | | 433/172 |
| 2016/0022391 | A1 * | 1/2016 | Ishiwata ................ | A61K 6/818 |
| | | | | 29/896.1 |

(Continued)

*Primary Examiner* — Matthew M Nelson
(74) *Attorney, Agent, or Firm* — Faegre Drinker Biddle & Reath LLP

(57) ABSTRACT

An approach is disclosed that involves creating an implant-supported prosthesis that is dynamically guided into position using an image-guided navigation system into position in a patient's mouth without the use of a surgical guide.

17 Claims, 7 Drawing Sheets

(56) References Cited

U.S. PATENT DOCUMENTS

| | | | |
|---|---|---|---|
| 2016/0074141 A1* | 3/2016 | Lozada | A61C 8/0089 |
| | | | 433/174 |
| 2017/0231730 A1* | 8/2017 | Shen | A61C 13/30 |
| | | | 433/201.1 |
| 2018/0064512 A1* | 3/2018 | Kim | A61C 8/0045 |
| 2018/0280121 A1* | 10/2018 | Zhang | A61C 13/2255 |
| 2019/0029778 A1* | 1/2019 | Miller | A61C 8/0048 |

* cited by examiner

METHOD FOR DYNAMICALLY GUIDING A DENTAL ORAL AND MAXILLOFACIAL PROSTHESIS

RELATED APPLICATIONS

This application is related to and claims priority from United States Provisional Application 62/737,539, filed Sep. 27, 2018, the disclosure of which is incorporated herein by reference in its entirety.

FIELD OF THE INVENTION

An improved dental/maxillofacial implant method and apparatus is disclosed, and, more particularly a dental and maxillofacial prosthesis that is guided into position to fit on the patient's jaw and maxillofacial structures without the use of a surgical guide. The method involves the use of an image-guided navigation system to determine the position of the prosthesis on the patient's jaw and maxillofacial region and placing the prosthesis accurately without the use of a physical surgical guide.

BACKGROUND

The use of surgical navigation in the head and neck has made significant advancements in the past few years. Presently, systems are used in otolaryngology, neurosurgery and oral and maxillofacial surgery for a variety of surgical procedures. Some examples of the existing technologies are disclosed in U.S. Pat. Nos. 9,943,374, 9,402,691, 9,844,324, the disclosures of which are each incorporated herein by reference in its entireties.

Recent advances allow dentists, oral and maxillofacial surgeons and maxillofacial prosthodontists to place dental implants accurately without the use of physical surgical guides using these image guided navigation systems. Once the implants are placed, relating a prefabricated dental and maxillofacial prosthesis to the implants has remained a challenge.

Physical guides are presently used to orient a pre-surgically fabricated prosthesis to the implants. The problem with these physical guides is that they require large incisions and complex fabrication techniques often utilizing stacked, indexed guides and frame sets. If the guides are not accurately aligned related to the bone they often do not fit the patient properly. In regions outside the oral cavity they are often impossible to place into the maxillofacial defect.

A need exists for an improved system for accurately and easily placing a prosthesis to an implant with minimal trauma to the patient.

SUMMARY OF THE INVENTION

A method for placing an implant supported fitted dental prosthesis in the oral and maxillofacial region is disclosed. The method comprises the steps of providing a prefabricated oral and maxillofacial prosthesis with an alignment support structure affixed to a surface of the prosthesis, and at least one fixation feature; using an image navigation system to dynamically navigate the surgical placement of at least one implant that is adapted to mate with the at least one fixation feature; and attaching the implant to the at least one fixation feature while the prosthesis is in or on the oral and maxillofacial region.

In an embodiment the at least one fixation feature is a predrilled hole and wherein the method involves the step of drilling a hole in the prosthesis.

Optionally, the method includes the step of providing an implant abutment and wherein the step of attaching the implant to the at least one fixation feature involves the step of adhering an implant abutment into the predrilled hole.

The method may include the step of forming one or more osteotomies in the patient's jaw and/or maxillofacial bones, wherein the alignment support structure includes one or more pins designed to mate with the one or more navigated osteotomies.

The alignment support structure may include one or more removable alignment features configured to contact existing hard tissue of the oral or maxillofacial anatomy when the prosthesis is properly located in the oral cavity or maxillofacial bones.

It is contemplated that the fixation feature may provide alignment for the alignment support structure.

In one embodiment an implant abutment sleeve mates with the fixation features to assist in alignment of the dental prosthesis in the oral cavity or maxillofacial region.

The method may involve the steps of measuring a final implant location based on an initial placement of the prosthesis in the oral cavity and maxillofacial area and modifying at least one of the at least one fixation feature based upon the measured final implant location.

A method for placing an implant supported fitted dental or maxillofacial prosthesis within or on any maxillofacial structure is disclosed that comprises the steps of providing a prefabricated implant supported prosthesis with an alignment support structure affixed to a surface of the prosthesis; using an image navigation system to dynamically navigate the surgical placement of at least one implant for its initial implant placement and measuring its final position; using the measured final position to place at least one fixation feature in the prefabricated dental or maxillofacial prosthesis; and attaching the implant to the at least one fixation feature.

The fixation feature may be milled into the prosthesis.

Alternatively or in addition the fixation feature may be drilled using a dynamically guided surgical instrument.

In any of the methods disclosed the step of measuring the final implant location may involve tracking the trajectory of a surgical instrument during the initial implant placement.

Optionally, the step of measuring the final implant location may involve scanning the oral cavity after initial implant placement.

In an embodiment, the step of scanning may comprise placing an implant fiducial on each implant, the implant fiducial configured to an intra oral or desktop prosthetic scanner to record the implant's exact location.

In an embodiment, the scanning may be a 3D radiological scan.

In an embodiment, the scanning may be a 3D optical intra-oral scan.

Optionally, the step of measuring the final implant locations involves optically locating the implants relative to a patient tracking fiducial using the dynamic navigation system.

A method for determining the final locations of a set of implants relative to a 3-dimensional dataset is disclosed. The method comprises the steps of providing a 3-dimensional dataset including planned locations of the implants; a set of implants surgically placed in a patient; a patient tracker attached to the patient; and a transform relating the patient tracker to the 3-dimensional dataset; using a tracking system to measure the locations of one or more of the implants simultaneously with the patient tracker; and communicating the final locations of the set of implants relative to the 3-dimensional dataset.

The foregoing and other features of the invention and advantages of the present invention will become more apparent in light of the following detailed description of the preferred embodiments, as illustrated in the accompanying figures. As will be realized, the invention is capable of modifications in various respects, all without departing from the invention. Accordingly, the drawings and the description are to be regarded as illustrative in nature, and not as restrictive.

BRIEF DESCRIPTION OF THE DRAWINGS

For the purpose of illustrating the invention, the drawings show a form of the invention that is presently preferred. However, it should be understood that the invention is not limited to the precise arrangement and instrumentalities show in the drawings. It should also be understood that the invention is not limited to the anatomic location illustrated but may be used in or on any maxillofacial structure suitable for the use of dental implants.

DETAILS DESCRIPTION OF THE INVENTION

Figure 1:
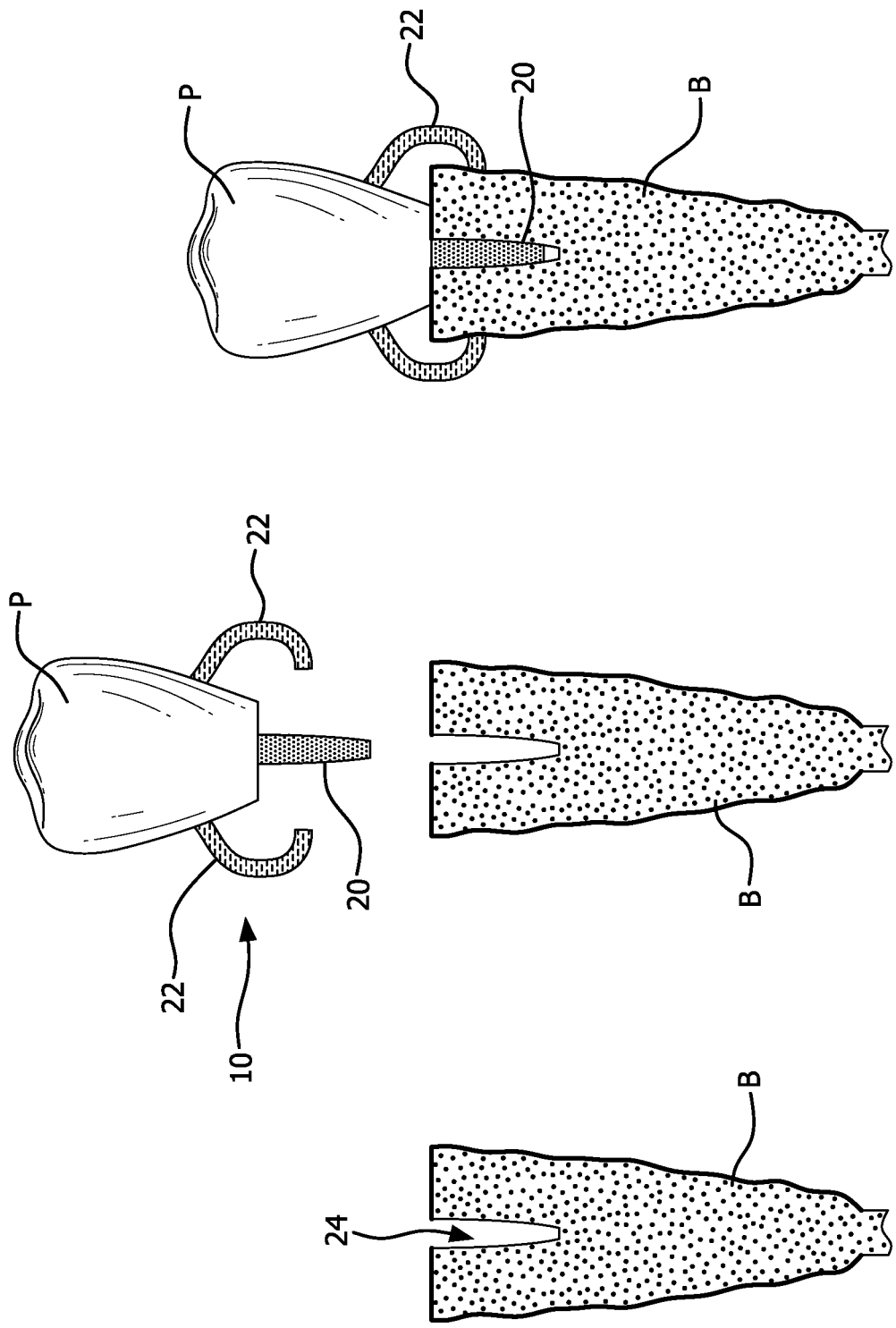
FIG. 1 is a cross-sectional view of a dynamically guided support structure according to the present invention shown in the stages of being mounted on a bone.

The present invention is directed to a system and method to allow a dentist to plan an implant position prior to surgery using a dynamic navigation system, plan the prosthesis related to the implant plan and then accurately relate the prosthesis to the patient's anatomy and the newly placed implants without the use of a physical surgical guide. Minimal incisions are used as no guides are necessary. In a preferred embodiment, the prosthesis includes an alignment support structure for assisting with the proper positioning of the prosthesis with respect to the patient anatomy during fitting, and one or more implant fixation systems for final fixation of the prosthesis to the anatomy, each of which consists of a fixation feature, which in the preferred embodiment is a hole in the prosthesis, an abutment that will be rigidly attached to the fixation feature, and an implant that will be drilled into the patient's bone and that will be removably mated to the abutment.

The system involves first obtaining a pre-surgical data set that is acquired from the patient through an image scanning. The pre-surgical digital data set is to be used by the dynamic image navigation system for planning the implant and then the prosthesis. This digital data set may be obtained using any conventional means, and may include a three dimensional radiograph; a computed tomogram or cone beam computed tomogram; an intraoral digital scan; digital scans of models; and/or digital photographs, either 2D or 3D.

To obtain the digital data set, a three dimensional radiograph is taken, preferably a cone beam computed tomogram (CBCT) taken with or without radiographic markers or fiducials attached rigidly to the patient's skeleton/bone structure in the area of the scan, either with screws or a removable device. If desired, a scanning appliance with markers/fiducials may be attached to the patient's mouth at the time of the radiograph to assist with the surgical planning. One type of appliance is disclosed in U.S. Pat. No. 9,402,691 the disclosure of which is incorporated herein by reference in its entirety. This appliance may be custom-made with fiducials or, alternatively, could be the patient's denture or a dental appliance that has fiducials attached. The CBCT may be taken with the patient's teeth touching, in occlusion, or with the teeth separated. If the patient has no teeth, the dentures or scanning appliance may or may not be touching or in occlusion. The radiograph is preferably stored in a digital imaging and communication (DICOM) format.

It is also contemplated that intra-oral optical scans may, optionally, be used in the surgical planning. Intra-oral scans are typically stored in a surface format consisting of a triangulated irregular network (TIN) of 3D points representing one or more surfaces of a patients anatomy. Intra-oral scans are typically registered via matching surface contour information with a surface extracted from the 3D radiograph. Intra-oral optical scans provide additional information about soft-tissue boundaries and are less susceptible to image artifacts that can lead to ambiguity in determining hard-tissue structure, so can assist in planning around the anatomical features. In addition, the invention contemplates the use of laser scans of physical models, which may or may not be used. These models may, for example be wax-ups of the desired restorative result, the patient's existing denture, or a provisional prosthesis.

Three- or two-dimensional photographs in digital format may also be used.

The digital files are brought into (accessed by) the image navigation system planning software. For example, the digital data files may be imported into the navigation system, or the software can access the digital data files from a stored location (which can be local or remote). The digital datasets are then registered to one another to bring them into a common coordinate system. The registration consists of spatially aligning common features of each imaging modality using a rigid-body transformation in order to minimize the spatial disparity between the common features once aligned. In the case of registering intra-oral scans to CBCT scans, this typically involves first extracting an isosurface or other surface estimate from the CBCT scan by analyzing high-gradient regions of the CBCT scan data, then determining an alignment between the surface estimate and the intra-oral scan data. 2D or 3D photos can also be registered to the 3D dataset by determining the relationship between coordinate system of the camera that produced them and the CBCT scan, which is done by determining correspondences between feature points in both modalities and using either a perspective N-points algorithm for 2D images, or an absolute orientation algorithm for 3D images. Alternative registration algorithms can be contemplated which similarly minimize the matching disparity between modalities.

Using the image navigation system planning software, the relevant anatomy is outlined and mapped to determine location of pertinent anatomy. The arch form, also referred to as the panoramic curve, can be manually marked by the doctor by marking control points at key locations (e.g., known tooth locations) along the patient's arch, and then connected using a spline curve. These splines can also be automatically detected based upon an algorithmic analysis of the CBCT data. Nerve canals can also be manually marked by the surgeon by defining control points in cross-sectional slices of the CBCT scan. The hard tissue (bone and teeth) is automatically segmented within the CBCT scan by analyzing the HU values in the CBCT scan to determine interfaces between hard tissue and soft tissue or air. This can also be performed with doctor in the loop, where the segmentation can be seeded or further refined by human interaction. Teeth and sinus can be further segmented based on anatomical atlas analysis and/or shape-prior analysis. Depending on the surgical location and procedure, other items of the patient's anatomy may be segmented either in a doctor-assisted manner or in a fully-automated way.

The doctor uses the image navigation system planning software to plan which implants to use and plan the locations for them, as well as the amount of bone reduction needed during the surgery. The level of the implant platforms, where the prosthesis will ultimately engage with the implants, is determined by considering the height of the desired prosthesis and the vertical engagement overlap between the prosthesis and the implants. The bone reduction is then planned to allow proper spacing between the bone and the desired prosthesis.

Next, the prosthesis is planned, with space for soft tissue under the prosthesis. Planning consists both of determining the position and angulation of the prosthesis, as well as its shape. Position and angulation can be manipulated by the doctor in the planning software by dragging the prosthesis in cross-sectional slices in the planning software. Shape can be defined based upon a scan of a wax-up, by the results of a design from a 3D modeling software, or by adjusting, stretching, and merging 3D models of virtual teeth with a portion of the bone anatomy extracted from the CBCT scan or intra-oral scan. The amount of vertical space for soft tissue must be noted. The size of the holes in the prosthesis will be calculated based upon the accuracy of the dynamic image navigation system. The following deviations are considered: Angular deviation; Horizontal coronal deviation; Horizontal apical deviation; and Vertical deviation.

Figure 7:
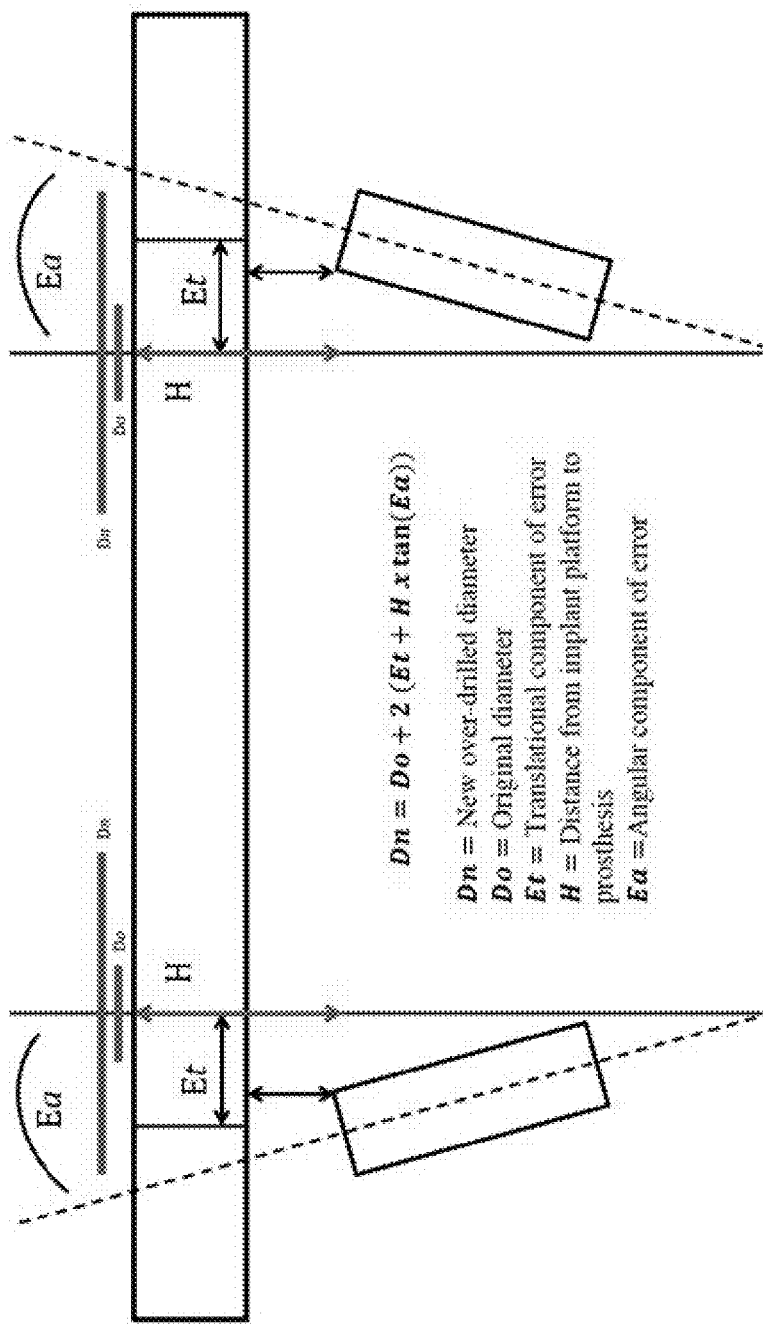
FIG. 7 is a schematic illustration of the calculations used to determine the size of the prosthetic holes as they relate to the dynamically guided navigation system.

The hole size is determined by using the following mathematical formula (Formula 1) incorporating the accuracy of the dynamic image navigation system, the vertical position of the planned prosthesis, the entry and exit of the implant components. See FIG. 7.

$$Dn = Do + 2\ (Et + H \times \tan(Ea)) \quad \text{Formula 1}$$

Where $Dn$=New over-drilled diameter
$Do$=Original diameter
$Et$=Translational component of error
$H$=Distance from implant platform to prosthesis
$Ea$=Angular component of error The system then calculates the attributes of the dynamically guided prosthesis to aid in manufacturing. Digital dynamically-guided prosthetic alignment support structure is planned. In a preferred embodiment, the alignment support structure is comprised of multiple alignment support systems. Referring to FIGS. 1-6, each support system 10 consists of a central pin 20 and two alignment features 22, which assist in aligning the prosthetic P in its proper orientation when placed in the patient's mouth. In a preferred embodiment, three or more of these support systems are used, and are spread throughout locations on the arch, for example one support system in the anterior and one support system posterior on each side of the arch. It is contemplated that the central pin(s) 20 will be located on the prosthesis P so as to contact areas on the bone B where implants 30 will not be placed. They may be placed mesial or distal to any planned implant below the planned prosthesis. Fewer support systems can be used if sufficient stability can be achieved. The support structure 10 may also consist of other arrangements and combinations of central pins and alignment features, or may consist of only central pins or alignment features. The central pin 20 is configured to project into the bone B, below the level of the planned implant platform, or the level of bone reduction, preferably by a minimum of 3 mm. The central pin's full length below the planned prosthesis is, therefore, calculated to be the length for accommodating soft tissue (if any) plus the projected length into the bone B below the level of the bone reduction or the platform height. A planned hole 24 is drilled into the patient's bone B (osteotomy) for the central pin 20 and is preferably larger than the pin, by a margin that is determined by the accuracy of the navigation system. This is calculated using the lateral and vertical margins of error of the navigation system.

On the buccal and lingual, or palatal and labial sides of the central pin 20, two alignment features 22 are provided. The alignment features preferably engage the bone surface B below the level of the planned implant platforms. The shape of these bone supports may vary but they preferably complement the shape of "virgin" bone to engage with it, and are sufficiently rigid to prevent distortion. Although the alignment features 22 are depicted as curved "arms" in the figures, it should be readily apparent that the alignment features could be tapered or straight "arms". The alignment features 22 are designed to provide temporary alignment and lateral support for the prosthesis Important anatomic structures should be avoided. Thus, the support system 10 for each prosthesis should be designed to accommodate these anatomic structures. In the preferred embodiment, the planned prosthesis is manufactured with the alignment support system incorporated directly into the prosthesis, and made out of the same material as the prosthetic, with the intention that the alignment features and central pins will be cut off once the surgery is complete.

At the time of surgery, small incisions are made to expose the sites of the implants and reduce the bone. The implant positions are navigated using the dynamic image-guided navigation system and the surgical plan, and the osteotomies for the central pins of the alignment support system are navigated and holes drilled into the bone. The implants 30 are then placed in the bone. The implants and implant abutment 34 form a two-piece attachment mechanism that will provide the long-term attachment between the bone and the prosthetic once the alignment support system is removed. Implants and abutments are well known and, therefore, no detailed discussion is necessary. The implants 30 will remain screwed into and engage the bone, and typically have a female internal mounting thread. The abutments 34 are typically designed to be removably screwed into the implant 30 via a screw (not shown) through the abutment which engages with the internal implant threads.

Figure 2:
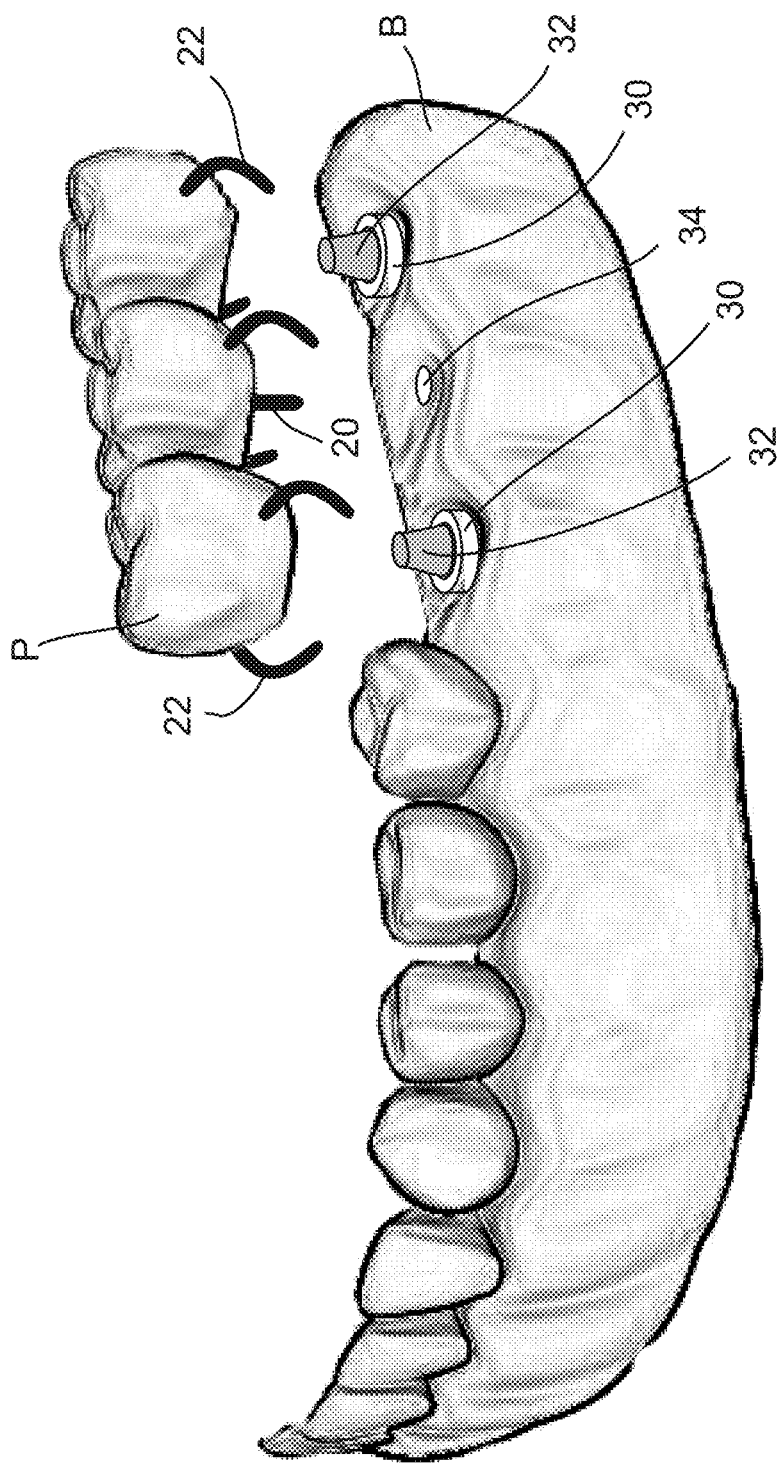
FIG. 2 is a perspective view of a portion of a patient's jaw illustrating one embodiment of an alignment support system for locating a prosthesis on multiple implants with abutments for the implants located on the implants before attachment.
Figure 3:
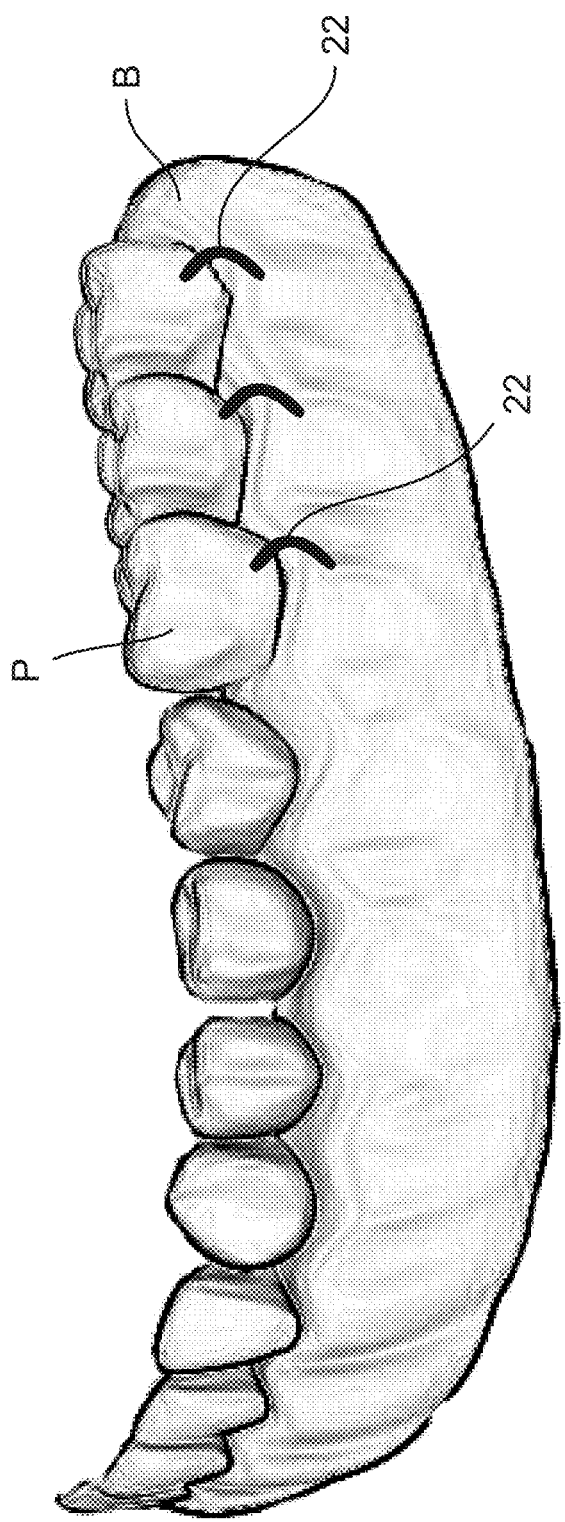
FIG. 3 is a perspective view of a portion of a patient's jaw illustrating one embodiment of the alignment support system for FIG. 2 as it provides guidance on placement of the prosthesis.

There are many other implant/abutment systems and the attachment mechanism varies widely. Once the implant 30 has been placed, the prefabricated implant abutments 32 are then temporarily attached to the implants 30. FIG. 2. The abutments 32 will ultimately be glued into holes in the prosthetic, and will be the mechanism by which the prosthetic is attached to the implants 30, but attaching the abutment 32 to the implant 30 at this point ensures that the abutments 32 will be properly aligned to their respective implants 30 once the abutments 32 have been glued in place in the prosthetic P. The prefabricated prosthesis P is placed over the abutments 32 and the central pin(s) 20 are engaged in their appropriate bone holes 24 (osteotomies). FIG. 3. The buccal and lingual, palatal and labial alignment features 22 of the alignment support system are then pushed into contact with the bone B, which helps to set the final vertical position with respect to the bone. The patient is placed in their final bite, occlusion, so that the patient's opposing dentition comes in contact with and aligns with complementary occlusal surface of the prosthesis. This bite forces the prosthesis to move into a position where the occlusion happens at many points to provide the best level of comfort to the patient. Once in occlusion, a dental adhesive material is injected into the holes in the prosthesis to affix the prosthesis to the abutments in order to fix the prosthesis in its final position.

Figure 4:
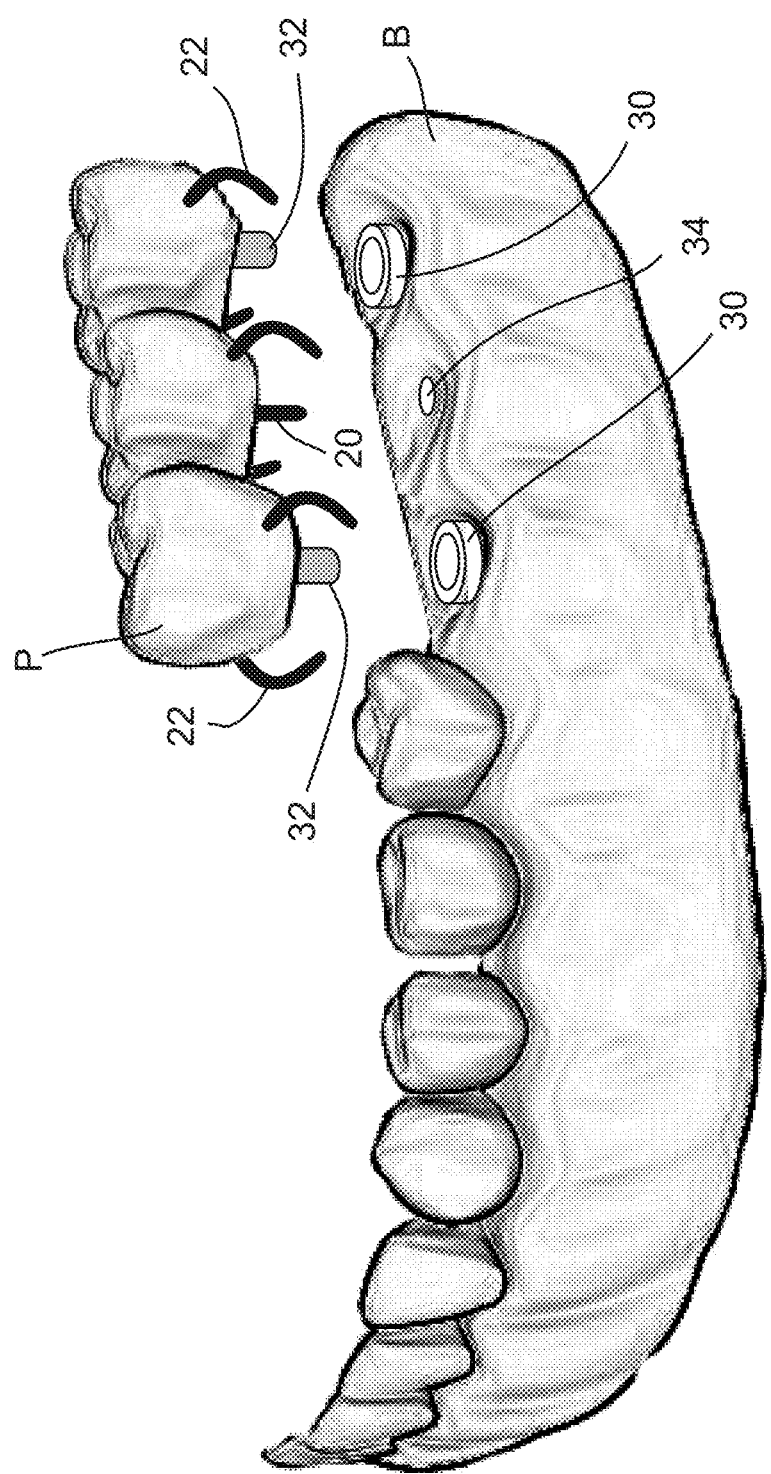
FIG. 4 is a perspective view of a portion of a patient's jaw illustrating the prosthesis of FIG. 3 with the abutments attached to the prosthesis.
Figure 5:
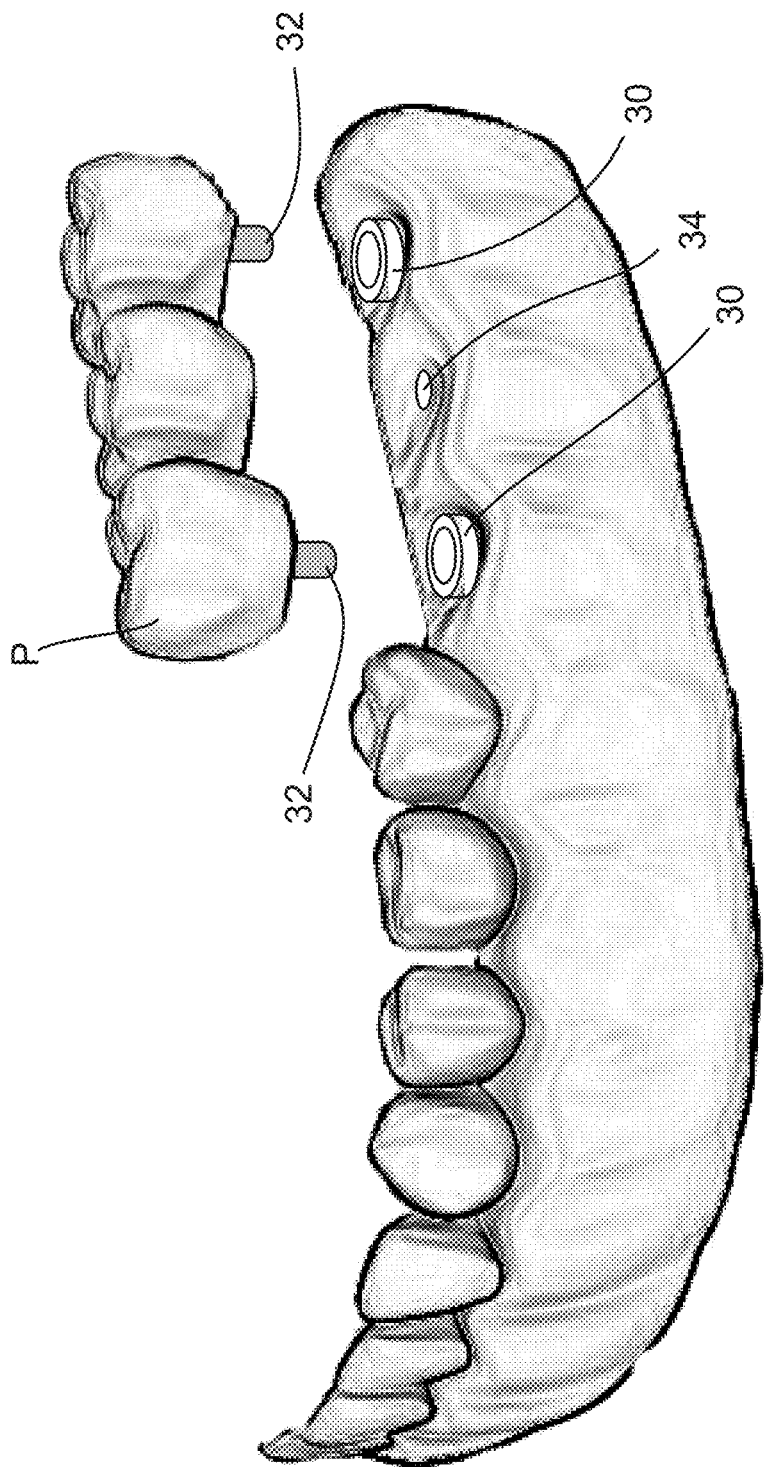
FIG. 5 is a perspective view of a portion of a patient's jaw illustrating the prosthesis of FIG. 4 with the alignment support system removed.
Figure 6:
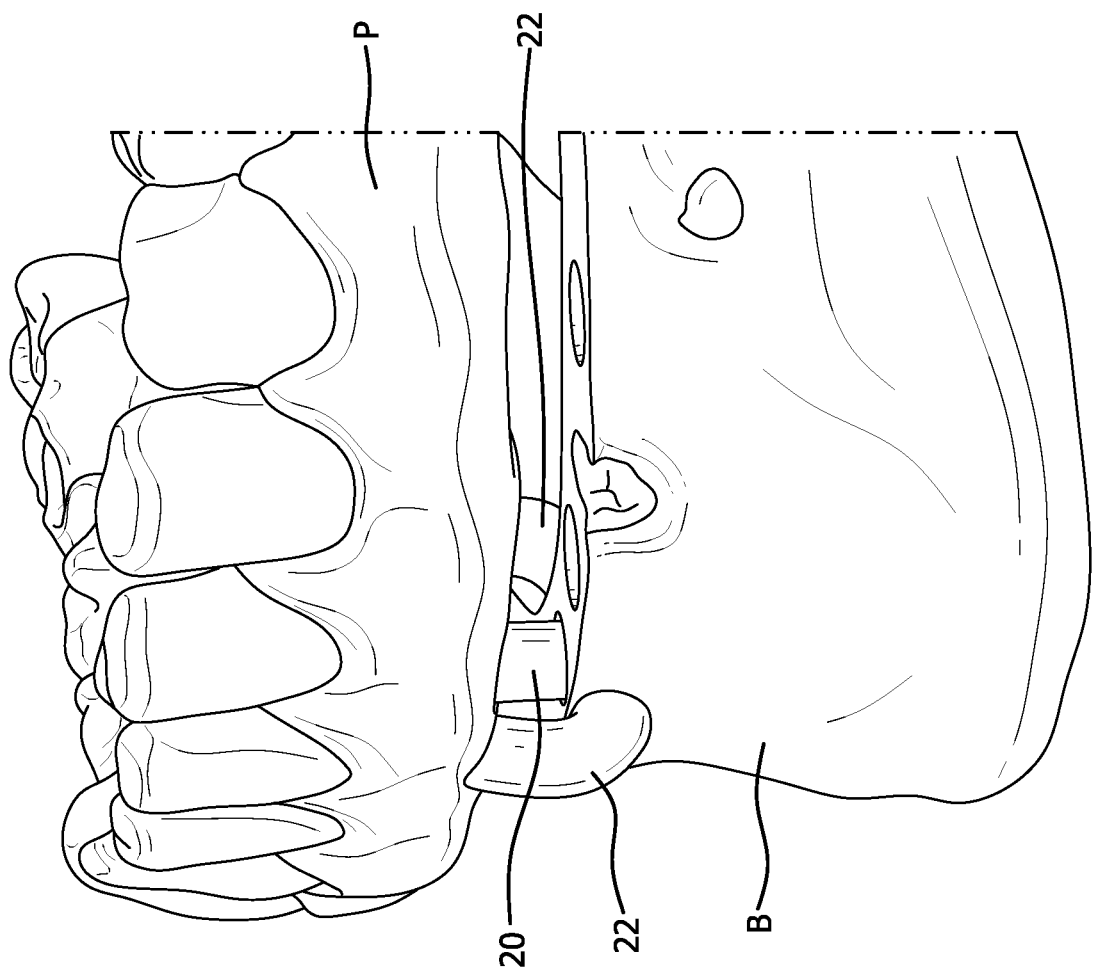
FIG. 6 is a perspective view of a portion of a patient's jaw illustrating one embodiment of an alignment support system for locating a prosthesis in place on the jaw with the alignment support system attached.

Once the adhesive material has set, the abutments are detached from the implants. FIG. 4. The prosthesis, and its now-fixed abutments are removed from the mouth and the alignment support systems are removed from the prosthesis by cutting using dental instruments. FIG. 5. The prosthesis is then finished and put in place. FIG. 6.

Numerous alternate embodiments exist.

In one such embodiment, the prosthesis can be manufactured prior to the surgery without the prosthetic holes. The prosthetic holes can then be milled in the doctor's office before or after placing the implants. The holes can accurately be drilled by using the same tracking system as used for guidance of the osteotomy, by first attaching a tracking fiducial to the prosthesis and then registering the prosthesis to the tracking system, which can be performed e.g., by using a keyed connection to the tracking fiducial, or by touching or scanning over portions of the prosthesis with a tracked surgical instrument. Alternately, the prosthetic holes could be made using an in-office milling machine, which could be simplified by incorporating mechanical registration features to reproducibly place the prosthesis into a known alignment within the milling machine prior to milling. In-office drilling of the prosthesis holes has the advantage that the implant plan may be changed on the day of surgery if surgical conditions find that the initially planned implant locations are not clinically acceptable.

In a further embodiment, the shapes and locations of the prosthetic holes can be determined by measuring the final implant locations rather than by using the planned implant locations. In the measurement process, the surgeon would first attach an implant fiducial onto each of the placed implants, using a keyed attachment mechanism that is designed to mate with the implant's attachment system in the same way that implant abutments attach to implants. The surgeon then positions the tracking system relative to the patient such that each tracking fiducial can be measured simultaneously with, and relative to the patient tracking fiducial. It should be noted that each implant tracking fiducial does not necessarily need to be measured simultaneously with each other, only with the patient tracking fiducial. This measurement, in combination with the patient tracker registration, allows for determining the final location of each implant relative to the original DICOM coordinate system that formed the basis of the prosthesis design. An example of such a patient tracking system and patient tracking fiducial is described in more detail in U.S. Pat. No. 9,943,374. The implant fiducial on each implant could be a small plate with a printed pattern of corners or dots, a constellation of 3 or more reflective spheres, which would be tracked using triangulation of feature points. Alternately, the implant fiducial could be a unique, asymmetric shape, such as a scan body, whose shape could be reconstructed by the stereo tracking system and matched to the fiducial's geometric model using, for example, the iterated closest points (ICP) algorithm. In a further embodiment, the tracking system could track the shape of the protruding portion of the implant itself, rather than using a separate implant fiducial. The computational complexity of measuring the tracking fiducial locations can be reduced by using the planned implant locations to cue the system where to look for the tracking fiducials. Once the patient tracking fiducial has been identified, the 3D locations of the planned implant locations are known and can be projected into the tracking system's image coordinates, allowing a search to take place only in the neighborhood of those locations in the images, or if using ICP, allows the iteration to begin with the model in its planned location and to converge to its final measured location. One advantage of measuring the final implant location is that this removes the component of error associated with the surgeon's skill at following their plan, which leaves only the tracking system's intrinsic error, which is generally smaller and, therefore, allows the prosthetic holes to be oversized by a smaller margin. An intra-oral scanner can also be used for measuring final implant locations instead of a dynamic navigation system. The scanner will reconstruct the surface of the dental anatomy, along with the surfaces of scan bodies attached to the implants. Identifying the scan bodies in the intra-oral scan and registering these surfaces to the anatomical surfaces in the CBCT scan allows the final implant locations to be computed with respect to the DICOM coordinate system.

In a further embodiment, the holes would not be present in the prefabricated prosthetic, so they could instead be determined at the time of surgery. Once final implant locations are measured, the surgeon could then drill new holes using the tracking system, or have the holes milled. Similarly, the surgeon could enlarge existing prosthetic holes if the final implant positions shifted from their planned locations by more than the tolerance of the holes allows, The process of measuring final implant locations and enlarging holes could be an optional follow-up step performed if the prosthetic is found to not seat properly due to excessive implant placement error by the surgeon.

Variations of the alignment support system can be used. The central pin may be omitted. Instead, implant abutment sleeves, which are typically smooth-walled plastic sleeves that attach to the top of the abutment using a retention screw, can be used for lateral alignment stability when setting occlusion. These abutment sleeves would mate with complementary features machined into the prosthesis. Alternately, different pins may be used, e.g., removable and re-useable pins could be used and could be made of titanium or other materials. The alignment features can also be made of different materials and attached into the prosthetic. The mating system for these alignment features could allow for re-usable alignment of varying sizes, which would allow the user to fine-tune the fit by adjusting to shorter or longer supports or supports with different curvatures if, for example, the prosthesis cannot be brought into occlusion as planned.

In a further embodiment, the alignment support system could be dynamic, rather than a mechanical alignment system. In this approach, the prosthesis can be brought into occlusion and temporarily affixed to the opposing dentition in occlusion. The jaw position could then be manipulated until the prosthesis is in the desired position relative to the surgical jaw. The tracking system would determine the position by measuring a tracking fiducial attached to the surgical jaw simultaneously with a tracking fiducial attached to the prosthesis, and would provide feedback to assist in properly positioning the mandible to bring the prosthesis and the surgical jaw into proper (as-planned) alignment. Once in alignment, the prosthesis would be affixed to the abutments by injecting dental material into the holes, thereby preserving the desired alignment. This process could be assisted by using materials to shim the prosthesis so it would remain more stable while the dental material cures in the holes.

Variations in the prosthesis can be foreseen. The prosthesis can be machined from various materials, including ceramics such as Zirconia, plastics such as PEEK, PMMA, and composite materials. The prosthesis could also be grown using 3D printing method as known to those skilled in the art. The prosthesis could include integrated metal support structures e.g., to support the alignment support pins or to support a keyed tracking fiducial, or could include machined fiducial touch features that would allow the surgeon to touch the fiducial features with a tracked instrument in order to assist the surgeon in registering the alignment of the prosthesis to an attached tracking fiducial.

Variations in the dynamic guidance system can be used. Optical tracking systems, based on multi-camera triangulation or monocular triangulation, time of flight, or wave-front technologies could be used, as well as electromagnetic tracking, inertial sensing, ultrasonic or field effect technologies could be used. Likewise, robotic navigation systems can be used to assist in drilling the actual osteotomies and the holes in the prosthetic. This would have the benefit of reducing the component of error due to the surgeon's ability to follow the implant plan, which would result in the holes being oversized by a smaller margin.

While the present invention has been described for placing a fitted dental prosthesis within an oral cavity, the invention can also be used to attach any implant supported maxillofacial prosthesis within or on any maxillofacial structure, for example, eye, nose, ear, maxilla, mandible, zygoma or frontal bone.

The system or systems described herein may be implemented on any form of computer or computers and the algorithms and programs may be implemented as dedicated applications or in client-server architectures, including a web-based architecture, and can include functional programs, codes, and code segments. The computer system of the present invention may include a software program be stored on a computer and/or storage device (e.g., mediums), and/or may be executed through a network. The computer steps may be implemented through program code or program modules stored on a storage medium.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The computer processes herein may be described in terms of various processing steps. Such processing steps may be realized by any number of hardware and/or software components that perform the specified functions. For example, the described embodiments may employ various integrated circuit components, e.g., memory elements, processing elements, logic elements, look-up tables, and the like, which may carry out a variety of functions under the control of one or more microprocessors or other control devices. Similarly, where the elements of the described embodiments are implemented using software programming or software elements the invention may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the embodiments of the invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail.

Finally, the steps of all methods described herein are performable in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

The invention claimed is:

1. A method for placing an implant supported fitted dental prosthesis in the oral or maxillofacial region, the method comprising the steps of:
   a. providing a prosthesis including a surface, the surface of the prosthesis having an alignment support structure affixed thereto and including at least one fixation feature;
   b. providing an implant that is a prefabricated oral or maxillofacial implant, the implant being configured to mate with the at least one fixation feature of the prosthesis; and
   c. placing the prosthesis on the implant via the at least one fixation feature and alignment support structure while the implant is in or on the oral or maxillofacial region by using an image navigation system to dynamically navigate the prosthesis to a predetermined position on the implant.

2. The method of claim 1, wherein providing the prosthesis includes predrilling a hole in the prosthesis, wherein the hole is the at least one fixation feature of the prosthesis.

3. The method of claim 2, further comprising providing an implant abutment, wherein attaching the implant to the at least one fixation feature includes adhering the implant abutment into the predrilled hole.

4. The method of claim 1, wherein the alignment support structure includes one or more pins, and wherein, when one or more osteotomies in the patent's jaw and/or maxillofacial bones is formed, the one or more pins is configured to mate with the one or more osteotomies.

5. The method of claim 1, wherein the alignment support structure includes one or more removable alignment features configured to contact existing hard tissue of oral or maxillofacial anatomy when the prosthesis is properly located in the oral or maxillofacial region.

6. The method of claim 1, wherein the at least one fixation feature and the alignment support structure share a portion of the surface of the prosthesis.

7. The method of claim 6, wherein a surface of an implant abutment sleeve contacts a surface of the fixation features to assist in alignment of the prosthesis in the oral or maxillofacial region.

8. The method of claim 1, further comprising measuring a final implant location based on an initial placement of the prosthesis in the oral and maxillofacial region and modifying at least one of the at least one fixation feature based upon the final implant location.

9. A method for placing an implant supported fitted dental or maxillofacial prosthesis into a patient's oral cavity or maxillofacial area, the method comprising the steps of:
  a. providing a prosthesis including a surface, the surface of the prosthesis having an alignment support structure affixed thereto;
  b. providing an implant that is a prefabricated oral or maxillofacial implant;
  c. dynamically navigating the prosthesis to an initial implant position via an image navigation system;
  d. measuring the initial implant position to determine a final implant position of the implant;
  e. using the final implant position as measured to place at least one fixation feature in the prosthesis; and
  f. attaching the implant to the at least one fixation feature.

10. The method of claim 9, wherein the at least one fixation feature is milled.

11. The method of claim 9, wherein the at least one fixation feature is drilled using a dynamically guided surgical instrument.

12. The method of claim 9, wherein measuring the final implant position includes tracking a trajectory of a surgical instrument while dynamically navigating the implant to the initial implant position.

13. The method of claim 9, wherein measuring the final implant position of the implant includes scanning an oral cavity of a patient after the implant is in the initial implant position.

14. The method of claim 13, wherein scanning the oral cavity includes placing an implant fiducial on the implant, the implant fiducial configured to an intra oral or desktop prosthetic scanner to record the implant's exact location.

15. The method of claim 14, wherein the scanning provides a 3D optical intra-oral scan.

16. The method of claim 13, wherein the scanning provides a 3D radiological scan.

17. The method of claim 9, wherein measuring the final implant position of the implant includes optically locating the implant relative to a patient tracking fiducial using the image navigation system.

* * * * *

UNITED STATES PATENT AND TRADEMARK OFFICE
CERTIFICATE OF CORRECTION

| | | |
|---|---|---|
| PATENT NO. | : 11,771,537 B2 | Page 1 of 1 |
| APPLICATION NO. | : 16/582666 | |
| DATED | : October 3, 2023 | |
| INVENTOR(S) | : Robert W. Emery, III, Scott A. Merritt and Lars Hansson | |

It is certified that error appears in the above-identified patent and that said Letters Patent is hereby corrected as shown below:

On the Title Page

Please replace Item (54) Title, and in the Specification, Column 1, Line 2, with the following:
-- METHOD FOR DYNAMICALLY GUIDING A DENTAL ORAL AND MAXILLOFACIAL PROSTHESIS --

Signed and Sealed this
Thirtieth Day of January, 2024

*Katherine Kelly Vidal*

Katherine Kelly Vidal
*Director of the United States Patent and Trademark Office*